(12) United States Patent
Shu et al.

(10) Patent No.: US 12,232,890 B2
(45) Date of Patent: Feb. 25, 2025

(54) ELECTROCARDIOGRAM (ECG) SIGNAL QUALITY EVALUATION METHOD BASED ON MULTI-SCALE CONVOLUTIONAL AND DENSELY CONNECTED NETWORK

(71) Applicants: Qilu University of Technology (Shandong Academy of Sciences), Jinan (CN); SHANDONG COMPUTER SCIENCE CENTER (NATIONAL SUPERCOMPUTING CENTER IN JINAN), Jinan (CN)

(72) Inventors: Minglei Shu, Jinan (CN); Rui Qu, Jinan (CN); Pengyao Xu, Jinan (CN); Shuwang Zhou, Jinan (CN); Zhaoyang Liu, Jinan (CN)

(73) Assignees: QILU UNIVERSITY OF TECHNOLOGY (SHANDONG ACADEMY OF SCIENCES), Jinan (CN); SHANDONG COMPUTER SCIENCE CENTER (NATIONAL SUPERCOMPUTING CENTER IN JINAN), Jinan (CN)

(*) Notice: Subject to any disclaimer, the term of this patent is extended or adjusted under 35 U.S.C. 154(b) by 0 days.

(21) Appl. No.: 18/398,263

(22) Filed: Dec. 28, 2023

(65) Prior Publication Data

US 2025/0009306 A1 Jan. 9, 2025

(30) Foreign Application Priority Data

Jul. 6, 2023 (CN) .......................... 202310822941.2

(51) Int. Cl.
*A61B 5/00* (2006.01)
*A61B 5/308* (2021.01)
*G06N 3/0464* (2023.01)

(52) U.S. Cl.
CPC ............ *A61B 5/7221* (2013.01); *A61B 5/308* (2021.01); *A61B 5/7203* (2013.01); *G06N 3/0464* (2023.01)

(58) Field of Classification Search
CPC ..... A61B 5/7221; A61B 5/308; A61B 5/7203; G06N 3/0464
See application file for complete search history.

(56) References Cited

U.S. PATENT DOCUMENTS

| | | | |
|---|---|---|---|
| 2020/0222018 A1* | 7/2020 | van Walsum | A61B 6/5264 |
| 2022/0361799 A1 | 11/2022 | Hong et al. | |
| 2024/0188895 A1* | 6/2024 | Zhang | A61B 5/7267 |

FOREIGN PATENT DOCUMENTS

| | | |
|---|---|---|
| CN | 110458245 A | 11/2019 |
| CN | 112971795 A | 6/2021 |

(Continued)

OTHER PUBLICATIONS

Wulan, Naren, et al. "Generating electrocardiogram signals by deep learning." Neurocomputing 404 (2020): 122-136. (Year: 2020).*

(Continued)

*Primary Examiner* — Miranda M Huang
*Assistant Examiner* — Sidney Vincent Bostwick
(74) *Attorney, Agent, or Firm* — Bayramoglu Law Offices LLC

(57) ABSTRACT

An electrocardiograph (ECG) signal quality evaluation method based on a multi-scale convolutional and densely connected network is provided. Firstly, an original ECG signal is preprocessed to remove a baseline drift and power line interference. Then, based on a consistency principle of a label determining result and a principle of setting a confidence coefficient, an AlexNet model is trained to mutually correct incorrect labels in a dataset to obtain a final ECG signal fragment for quality classification. Finally, the signal (Continued)

fragment is input into an improved lightweight densely connected quality classification model to classify quality of the ECG signal fragment.

9 Claims, 7 Drawing Sheets

(56) References Cited

FOREIGN PATENT DOCUMENTS

| | | |
|---|---|---|
| CN | 116350233 A | 6/2023 |
| WO | 2019100560 A1 | 5/2019 |

OTHER PUBLICATIONS

Zhang, Peng, et al. "Global hybrid multi-scale convolutional network for accurate and robust detection of atrial fibrillation using single-lead ECG recordings." Computers in Biology and Medicine 139 (2021): 104880. (Year: 2021).*

* cited by examiner

ELECTROCARDIOGRAM (ECG) SIGNAL QUALITY EVALUATION METHOD BASED ON MULTI-SCALE CONVOLUTIONAL AND DENSELY CONNECTED NETWORK

CROSS-REFERENCE TO THE RELATED APPLICATIONS

This application is based upon and claims priority to Chinese Patent Application No. 202310822941.2, filed on Jul. 6, 2023, the entire contents of which are incorporated herein by reference.

TECHNICAL FIELD

The present disclosure relates to the technical field of electrocardiograph (ECG) signal processing, and specifically, to an ECG signal quality evaluation method based on a multi-scale convolutional and densely connected network.

BACKGROUND

ECG signals collected by wearable or portable ECG monitoring devices may have different or inconsistent quality. Therefore, it is of great significance to evaluate the quality of the ECG signal. Most of current ECG signal quality evaluation methods proposed mainly evaluate quality of an entire signal. These methods have certain limitations in accurately evaluating quality of a signal fragment and extracting an important feature of a local signal. In addition, a current neural network used for quality evaluation has a large number of parameters and a large amount of computation. In order to meet a real-time requirement, a lightweight model needs to be constructed for quality evaluation of a signal obtained by a portable or wearable device.

SUMMARY

In order to overcome the shortcomings of the above technologies, the present disclosure provides a method for classifying quality of a signal fragment using an auxiliary label.

The technical solutions used in the present disclosure to resolve the technical problem thereof are as follows:

An ECG signal quality evaluation method based on a multi-scale convolutional and densely connected network includes:

a) obtaining n original ECG signals and corresponding labels thereof in a dataset to obtain an original ECG signal set S, where $S=\{s_1, s_2, \ldots, s_k, \ldots, s_n\}$, $s_k$ represents a $k^{th}$ ECG signal, $k \in \{1, 2, \ldots, n\}$, a corresponding label of the $k^{th}$ ECG signal $s_k$ is $l_k$, an ECG signal label set is L, and $L=\{l_1, l_2, \ldots, l_k, \ldots, l_n\}$;

b) preprocessing the $k^{th}$ ECG signal $s_k$ to remove a baseline drift and power line interference from the ECG signal $s_k$ to obtain a preprocessed ECG signal $x_k$, where a preprocessed ECG signal set is X, and $X=\{x_1, x_2, \ldots, x_k, \ldots, x_n\}$;

c) segmenting the preprocessed ECG signal $x_k$ to obtain i ECG signal fragments $\{x_k^1, x_k^2, \ldots, x_k^i\}$, where corresponding labels of the i ECG signal fragments $\{x_k^1, x_k^2, \ldots, x_k^i\}$ are $\{l_k^1, l_k^2, \ldots l_k^i\}$, and a segmented signal fragment set is $x_{seg}$, $X_{seg}=\{\{x_1^1, x_1^2, \ldots, x_1^i\}, \{x_2^1, x_2^2, \ldots, x_2^i\}, \ldots, \{x_k^1, x_k^2, \ldots, x_k^i\}, \ldots, \{x_n^1, x_n^2, \ldots, x_n^i\}\}$, a segmented signal label set is $L_{seg}$, and $L_{seg}=\{\{l_1^1, l_1^2, \ldots, l_1^i\}, \{l_2^1, l_2^2, \ldots, l_2^i\}, \ldots, \{l_k^1, l_k^2, \ldots, l_k^i\}, \ldots, \{l_n^1, l_n^2, \ldots, l_n^i\}\}$;

d) inputting each ECG signal fragment in the signal fragment set $X_{seg}$ into a trained AlexNet model to obtain an evaluation-specific ECG signal fragment set $X_{final}$; and e) establishing an improved lightweight densely connected quality classification model, and inputting an ECG signal fragment in the evaluation-specific ECG signal fragment set $X_{final}$ into the improved lightweight densely connected quality classification model to obtain a classification result.

Preferably, the dataset in the step a) is a Brno University of Technology ECG Quality Database (BUTQDB) dataset.

Further, in the step b), a high-pass filter with an order of 4 and a cutoff frequency of 0.5 Hz is used to remove the baseline drift from the $k^{th}$ ECG signal $s_k$, and notch filters with cutoff frequencies of 49.1 Hz and 50.6 Hz are used to remove the power line interference from the $k^{th}$ ECG signal $s_k$, to obtain the preprocessed ECG signal $x_k$.

Preferably, in the step c), the preprocessed ECG signal $x_k$ is segmented based on a time length of 1 second to obtain the i ECG signal fragments $\{x_k^1, x_k^2, \ldots, x_k^i\}$.

Further, the step d) includes the following substeps:

d-1) dividing the signal fragment set $X_{seg}$ and the corresponding segmented signal label set $L_{seg}$ into a dataset A and a dataset B according to a ratio of 1:1, where a signal set in the dataset A is $X_{seg\_A}$, a label set in the dataset A is $L_{seg\_A}$, a signal set in the dataset B is $X_{seg\_B}$, and a label set in the dataset B is $L_{seg\_B}$;

d-2) inputting each ECG signal fragment in the signal set $X_{seg\_A}$ into an AlexNet model, and training the AlexNet model by using an Adam optimizer based on a cross-entropy loss $L_{CE}$ to obtain an optimized model AlexNet'$_1$;

d-3) inputting each ECG signal fragment in the signal set $X_{seg\_B}$ into the AlexNet model, and training the AlexNet model by using the Adam optimizer based on the cross-entropy loss LC to obtain an optimized model AlexNet"$_2$;

d-4) inputting each ECG signal fragment in the signal set $X_{seg\_B}$ into the optimized model AlexNet'$_1$ to obtain a corrected first label of each ECG signal fragment; and if an original label of each ECG signal fragment in the label set $L_{seg\_B}$ is consistent with the first label, or the original label of each ECG signal fragment in the label set $L_{seg\_B}$ is inconsistent with the first label and the first label is greater than a confidence coefficient $Con_{thr}$, retaining the ECG signal fragment, where $Con_{thr}=0.9$; or if the original label of each ECG signal fragment in the label set $L_{seg\_B}$ is inconsistent with the first label and the first label is less than the confidence coefficient $Con_{thr}$, discarding the ECG signal fragment, where all retained ECG signal fragments form a retained signal fragment set $X'_{seg\_1}$;

d-5) inputting each ECG signal fragment in the signal set $X_{seg\_A}$ into the optimized model AlexNet"$_2$ to obtain a corrected second label of each ECG signal fragment; and if an original label of each ECG signal fragment in the label set $L_{seg\_A}$ is consistent with the second label, or the original label of each ECG signal fragment in the label set $L_{seg\_A}$ is inconsistent with the second label and the second label is greater than the confidence coefficient $Con_{thr}$, retaining the ECG signal fragment; or if the original label of each ECG signal fragment in the label set $L_{seg\_A}$ is inconsistent with the second label and the second label is less than the confidence coefficient Con$_{thr}$, discarding the ECG signal fragment, where all retained ECG signal fragments form a retained signal fragment set X"$_{seg\_1}$; and d-6) calculating the final quality evaluation-specific ECG signal fragment set X$_{final}$ according to a formula X$_{final}$=X'$_{seg\_1}$+X"$_{seg\_2}$.

Further, in the step d-2), a batch size is set to 512 when the AlexNet model is trained by using the Adam optimizer based on the cross-entropy loss L$_{CE}$; and in the step d-3), a batch size is set to 512 when the AlexNet model is trained by using the Adam optimizer based on the cross-entropy loss L$_{CE}$.

Further, the step e) includes the following substeps:

e-1) constituting the improved lightweight densely connected quality classification model by a feature extraction module and a classification module, where the feature extraction module is constituted by a first multi-scale channel attention module MCA$_1$, a second multi-scale channel attention module MCA$_2$, a third multi-scale channel attention module MCA$_3$, a first multi-scale feature densely connected module MFD$_1$, a second multi-scale feature densely connected module MFD$_2$, and a third multi-scale feature densely connected module MFD$_3$, and the classification module is constituted by a linear layer;

e-2) constituting the first multi-scale channel attention module MCA$_1$ by a first convolution unit, a second convolution unit, a third convolution unit, a squeeze-and-excitation (SE) attention module, and an average pooling layer, where the first convolution unit is sequentially constituted by a convolutional layer, a batch normalization (BN) layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer; inputting the ECG signal fragment in the evaluation-specific ECG signal fragment set X$_{final}$ into the first convolution unit to obtain a shallow feature signal X$_{mca1\_f_0}$; inputting the ECG signal fragment in the evaluation-specific ECG signal fragment set X$_{final}$ into the second convolution unit to obtain a shallow feature signal X$_{mca1\_f_1}$; inputting the ECG signal fragment in the evaluation-specific ECG signal fragment set X$_{final}$ into the third convolution unit to obtain a shallow feature signal X$_{mca1\_f_2}$; concatenating the shallow feature signal X$_{mca1\_f_0}$, the shallow feature signal X$_{mca1\_f_1}$, and the shallow feature signal X$_{mca1\_f_2}$ to obtain a feature signal X$_{mca1\_f_3}$; inputting the feature signal X$_{mca1\_f_3}$ into the SE attention module to obtain important feature information X$_{mca1\_f_{se}}$; and inputting the important feature information X$_{mca1\_f_{se}}$ into the average pooling layer to obtain a feature signal X$_{mca1\_f_4}$;

e-3) constituting the first multi-scale feature densely connected module MFD$_1$ by a first densely connected layer, a second densely connected layer, a third densely connected layer, a fourth densely connected layer, a fifth densely connected layer, and a sixth densely connected layer, where the first densely connected layer, the second densely connected layer, the third densely connected layer, the fourth densely connected layer, the fifth densely connected layer, and the sixth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer; inputting the feature signal X$_{mca1\_f_4}$ into the first densely connected layer to obtain a feature signal X$_{mfd1\_f_1}$; concatenating the feature signal X$_{mca1\_f_4}$ and the feature signal X$_{mfd1\_f_1}$, and then inputting a concatenated signal into the second densely connected layer to obtain a feature signal X$_{mfd1\_f_2}$; concatenating the feature signal X$_{mca1\_f_4}$, the feature signal X$_{mfd1\_f_1}$, and the feature signal X$_{mfd1\_f_2}$, and then inputting a concatenated signal into the third densely connected layer to obtain a feature signal X$_{mfd1\_f_3}$; concatenating the feature signal X$_{mca1\_f_4}$, the feature signal X$_{mfd1\_f_1}$, the feature signal X$_{mfd1\_f_2}$, and the feature signal X$_{mfd1\_f_3}$, and then inputting a concatenated signal into the fourth densely connected layer to obtain a feature signal X$_{mfd1\_f_4}$; concatenating the feature signal X$_{mca1\_f_4}$, the feature signal X$_{mfd1\_f_1}$, the feature signal X$_{mfd1\_f_2}$, the feature signal X$_{mfd1\_f_3}$, and the feature signal X$_{mfd1\_f_4}$, and inputting a concatenated signal into the fifth densely connected layer to obtain a feature signal X$_{mfd1\_f_5}$; and concatenating the feature signal X$_{mca1\_f_4}$, the feature signal X$_{mfd1\_f_1}$, the feature signal X$_{mfd1\_f_2}$, the feature signal X$_{mfd1\_f_3}$, the feature signal X$_{mfd1\_f_4}$, and the feature signal X$_{mfd1\_f_5}$, and then inputting a concatenated signal into the sixth densely connected layer to obtain a feature signal X$_{mfd1\_f_6}$;

e-4) constituting the second multi-scale channel attention module MCA$_2$ by a first convolution unit, a second convolution unit, a third convolution unit, an SE attention module, and an average pooling layer, where the first convolution unit is sequentially constituted by a convolutional layer, a BN layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer; inputting the feature signal X$_{mfd1\_f_6}$ into the first convolution unit to obtain a shallow feature signal X$_{mca2\_f_0}$; inputting the feature signal X$_{mfd1\_f_6}$ into the second convolution unit to obtain a shallow feature signal X$_{mca2\_f_1}$; inputting the feature signal X$_{mfd1\_f_6}$ into the third convolution unit to obtain a shallow feature signal X$_{mca2\_f_2}$ concatenating the shallow feature signal X$_{mca2\_f_0}$, the shallow feature signal X$_{mca2\_f_1}$, and the shallow feature signal X$_{mca2\_f_2}$ to obtain a feature signal X$_{mca2\_f_3}$; inputting the feature signal X$_{mca2\_f_3}$ into the SE attention module to obtain important feature information X$_{mca2\_f_{se}}$; and inputting the important feature information X$_{mca2\_f_{se}}$ into the average pooling layer to obtain a feature signal X$_{mca2\_f_4}$ e-5) constituting the second multi-scale feature densely connected module MFD$_2$ by a first densely connected layer, a second densely connected layer, a third densely connected layer, and a fourth densely connected layer, where the first densely connected layer, the second densely connected layer, the third densely connected layer, and the fourth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer; inputting the feature signal X$_{mca2\_f_4}$ into the first densely connected layer to obtain a feature signal $X'_{mfd2\_}f_1$; concatenating the feature signal $X_{mca2\_}f_4$ and the feature signal $X'_{mfd2\_}f_1$, and then inputting a concatenated signal into the second densely connected layer to obtain a feature signal $X'_{mfd2\_}f_2$; concatenating the feature signal $X_{mca2\_}f_4$, the feature signal $X'_{mfd2\_}f_1$, and the feature signal $X'_{mfd2\_}f_2$, and then inputting a concatenated signal into the third densely connected layer to obtain a feature signal $X'_{mfd2\_}f_3$; and concatenating the feature signal $X_{mca2\_}f_4$, the feature signal $X'_{mfd2\_}f_1$, the feature signal $X'_{mfd2\_}f_2$, and the feature signal $X'_{mfd2\_}f_3$, and then inputting a concatenated signal into the fourth densely connected layer to obtain a feature signal $X'_{mfd2\_}f_4$;

e-6) constituting the third multi-scale channel attention module $MCA_3$ by a first convolution unit, a second convolution unit, a third convolution unit, an SE attention module, and an average pooling layer, where the first convolution unit is sequentially constituted by a convolutional layer, a BN layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer; inputting the feature signal $X'_{mfd2\_}f_4$ into the first convolution unit to obtain a shallow feature signal $X_{mca3\_}f_0$; inputting the feature signal $X'_{mfd2\_}f_4$ into the second convolution unit to obtain a shallow feature signal $X_{mca3\_}f_1$; inputting the feature signal $X'_{mfd2\_}f_4$ into the third convolution unit to obtain a shallow feature signal $X_{mca3\_}f_2$ concatenating the shallow feature signal $X_{mca3\_}f_0$, the shallow feature signal $X_{mca3\_}f_1$, and the shallow feature signal $X_{mca3\_}f_2$ to obtain a feature signal $X_{mca3\_}f_3$; inputting the feature signal $X_{mca3\_}f_3$ into the SE attention module to obtain important feature information $X_{mca3\_}f_{se}$; and inputting the important feature information $X_{mca3\_}f_{se}$ into the average pooling layer to obtain a feature signal $X_{mca3\_}f_4$ e-7) constituting the third multi-scale feature densely connected module $MFD_3$ by a first densely connected layer, a second densely connected layer, a third densely connected layer, and a fourth densely connected layer, where the first densely connected layer, the second densely connected layer, the third densely connected layer, and the fourth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer; inputting the feature signal $X_{mca3\_}f_4$ into the first densely connected layer to obtain a feature signal $X''_{mfd3\_}f_1$; concatenating the feature signal $X_{mca3\_}f_4$ and the feature signal $X''_{mfd3\_}f_1$, and then inputting a concatenated signal into the second densely connected layer to obtain a feature signal $X''_{mfd3\_}f_2$; concatenating the feature signal $X_{mca3\_}f_4$, the feature signal $X''_{mfd3\_}f_1$, and the feature signal $X''_{mfd3\_}f_2$, and then inputting a concatenated signal into the third densely connected layer to obtain a feature signal $X''_{mfd3\_}f_3$; and concatenating the feature signal $X_{mca3\_}f_4$, the feature signal $X''_{mfd3\_}f_1$, the feature signal $X''_{mfd3\_}f_2$, and the feature signal $X''_{mfd3\_}f_3$, and then inputting a concatenated signal into the fourth densely connected layer to obtain a feature signal $X''_{mfd3\_}f_4$; and e-8) inputting the feature signal $X''_{mfd3\_}f_4$ into the classification module of the improved lightweight densely connected quality classification model to obtain the classification result, and setting a quantity of output neurons in the linear layer to 3.

Preferably, in the step e-2), the convolutional layer of the first convolution unit has a 1×7 convolution kernel, a step of 3, and 16 channels, the convolutional layer of the second convolution unit has a 1×5 convolution kernel, a step of 3, and 16 channels, the convolutional layer of the third convolution unit has a 1×3 convolution kernel, a step of 3, and 16 channels, and the average pooling layer has a 1×2 pooling kernel and a step of 2; in the step e-3), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3; the third dilated convolutional layer has a 1×5 convolution kernel, 8 channels, a dilation rate of 2, and a step of 3, with a padding of 1; and the fourth dilated convolutional layer has a 1×7 convolution kernel, 8 channels, a dilation rate of 4, and a step of 3, with a padding of 1; in the step e-4), the convolutional layer of the first convolution unit has a 1×7 convolution kernel, a step of 3, and 32 channels, the convolutional layer of the second convolution unit has a 1×5 convolution kernel, a step of 3, and 32 channels, the convolutional layer of the third convolution unit has a 1×3 convolution kernel, a step of 3, and 32 channels, and the average pooling layer has a 1×2 pooling kernel and a step of 2; in the step e-5), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3, the third dilated convolutional layer has a 1×5 convolution kernel, 8 channels, a dilation rate of 2, and a step of 3, with a padding of 1, and the fourth dilated convolutional layer has a 1×7 convolution kernel, 8 channels, a dilation rate of 4, and a step of 3, with a padding of 1; in the step e-6), the convolutional layer of the first convolution unit has a 1×7 convolution kernel, a step of 3, and 64 channels, the convolutional layer of the second convolution unit has a 1×5 convolution kernel, a step of 3, and 64 channels, the convolutional layer of the third convolution unit has a 1×3 convolution kernel, a step of 3, and 64 channels, and the average pooling layer has a 1×2 pooling kernel and a step of 2; and in the step e-7), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3, the third dilated convolutional layer has a 1×5 convolution kernel, 8 channels, a dilation rate of 2, and a step of 3, with a padding of 1, and the fourth dilated convolutional layer has a 1×7 convolution kernel, 8 channels, a dilation rate of 4, and a step of 3, with a padding of 1.

Further, the ECG signal quality evaluation method based on a multi-scale convolutional and densely connected network further includes: after the step e), training the improved lightweight densely connected quality classification model by using a cross-entropy loss function and a backpropagation algorithm.

Preferably, when the improved lightweight densely connected quality classification model is trained, an initial growth rate is set to 8 and a batch size is set to 512.

The present disclosure has following beneficial effects: Firstly, an original ECG signal is preprocessed to remove a baseline drift and power line interference. Then, based on a consistency principle of a label determining result and a principle of setting a confidence coefficient, an AlexNet model is trained to correct incorrect labels in a dataset to obtain a final ECG signal fragment for quality classification. Finally, the signal fragment is input into an improved lightweight densely connected quality classification model to classify quality of the ECG signal fragment. The improved lightweight densely connected quality classification model is constructed to evaluate quality of the ECG signal. This can effectively evaluate quality of a local signal and avoid discarding an entire ECG signal due to noise in a certain part of the signal. In addition, the proposed model achieves relatively optimal performance with least parameters and floating-point operations, meeting a demand for real-time quality evaluation on a signal obtained by using a portable or wearable signal.

DETAILED DESCRIPTION OF THE EMBODIMENTS

Figure 1:
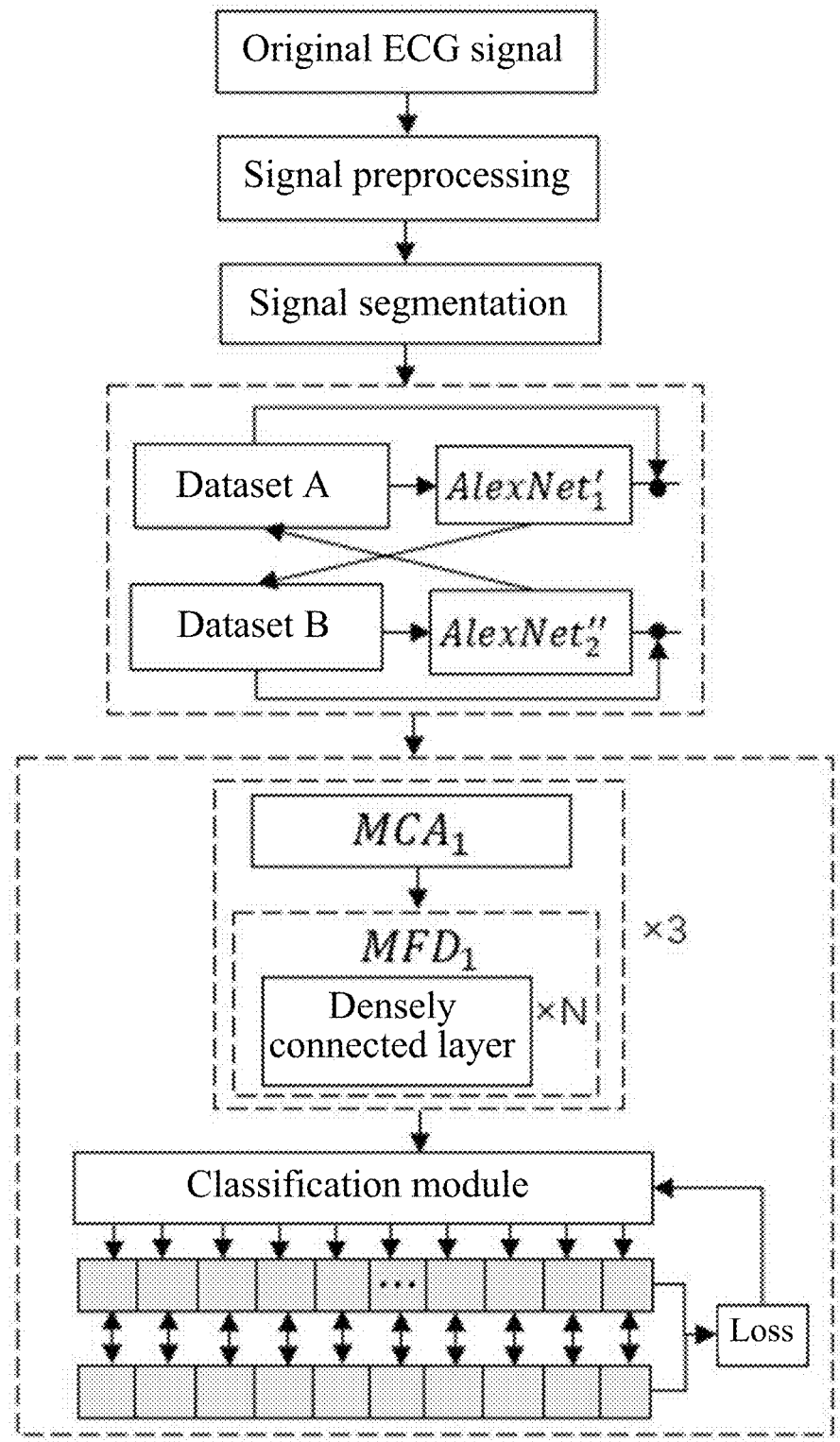
FIG. 1 is a flowchart of a method according to the present disclosure.
Figure 2A:
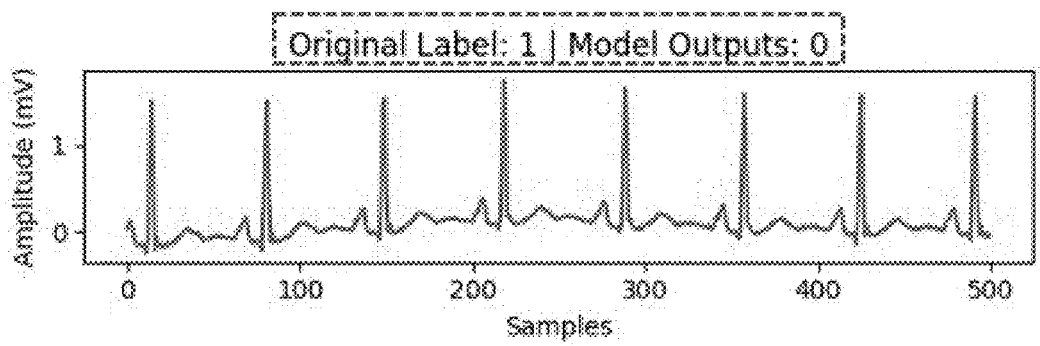
FIGS. 2A-2F show label comparison results before and after re-labeling.
Figure 2B:
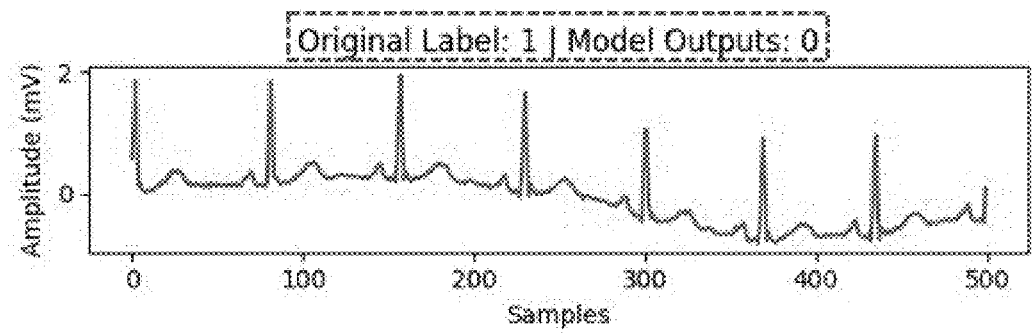
Figure 2C:
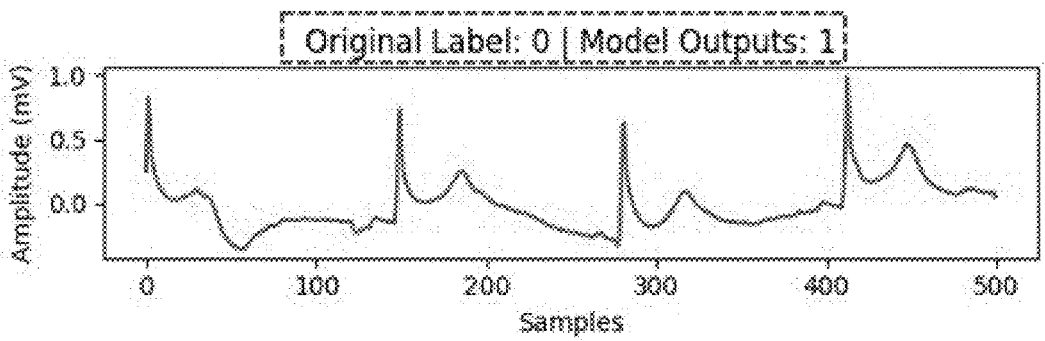
Figure 2D:
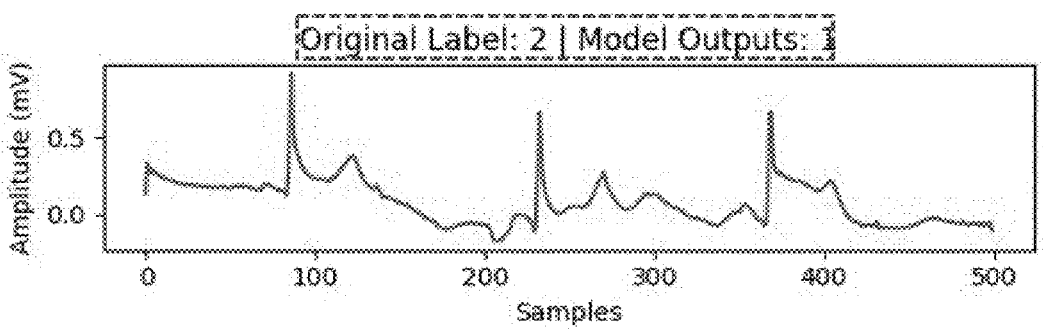
Figure 2E:
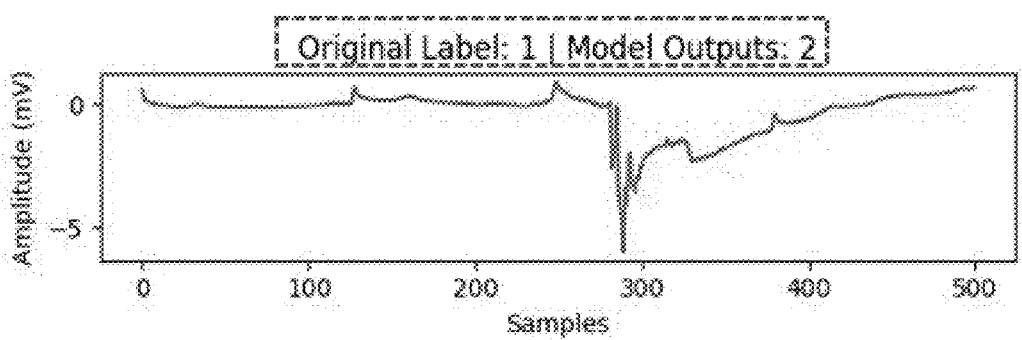
Figure 2F:
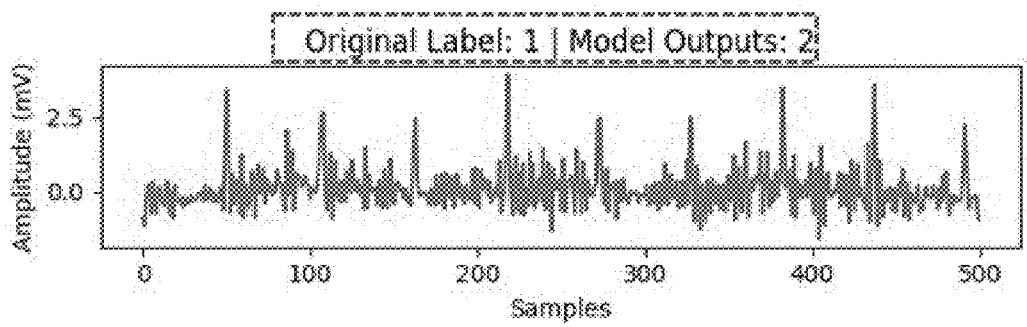
Figure 3A:
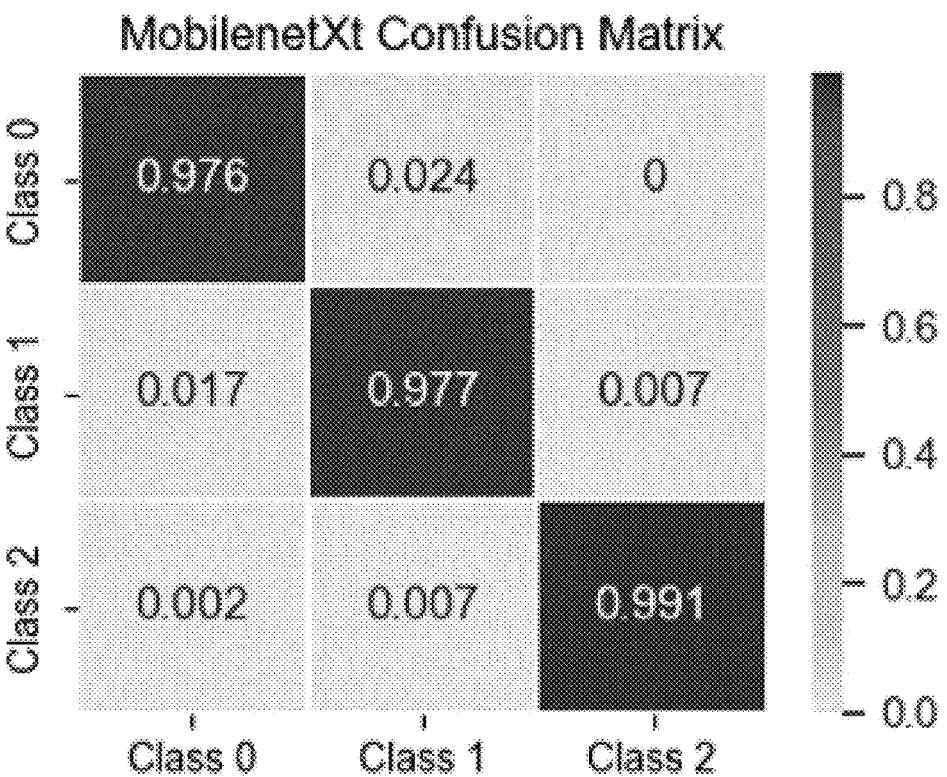
FIGS. 3A-3F compare confusion matrices for different models.
Figure 3B:
Figure 3C:
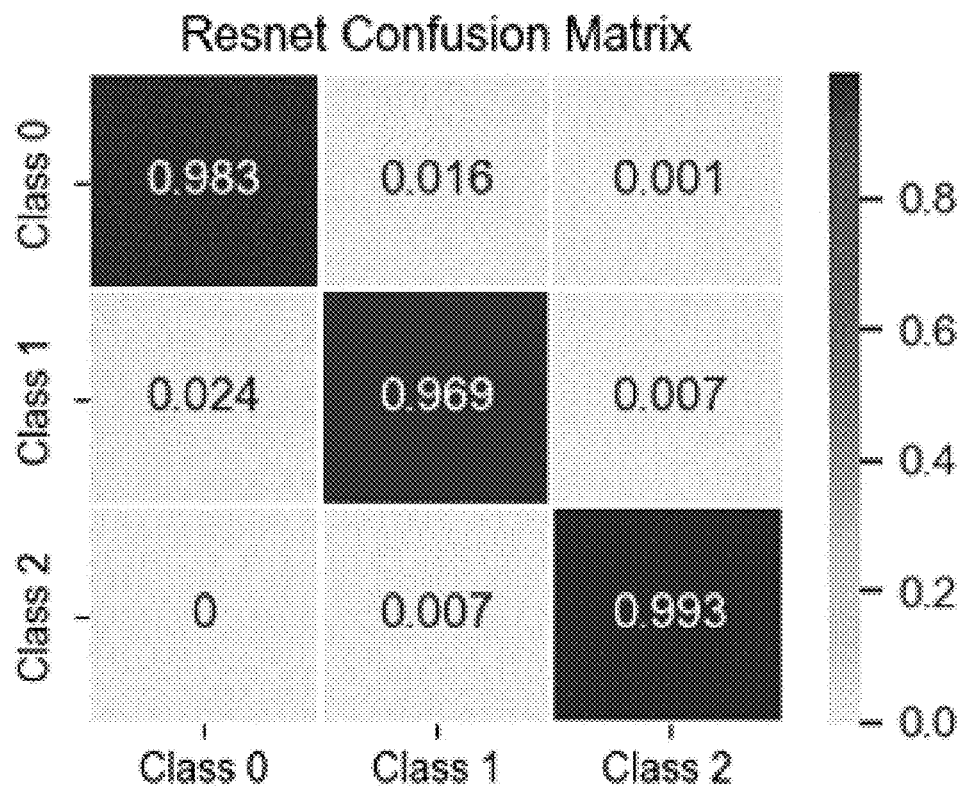
Figure 3D:
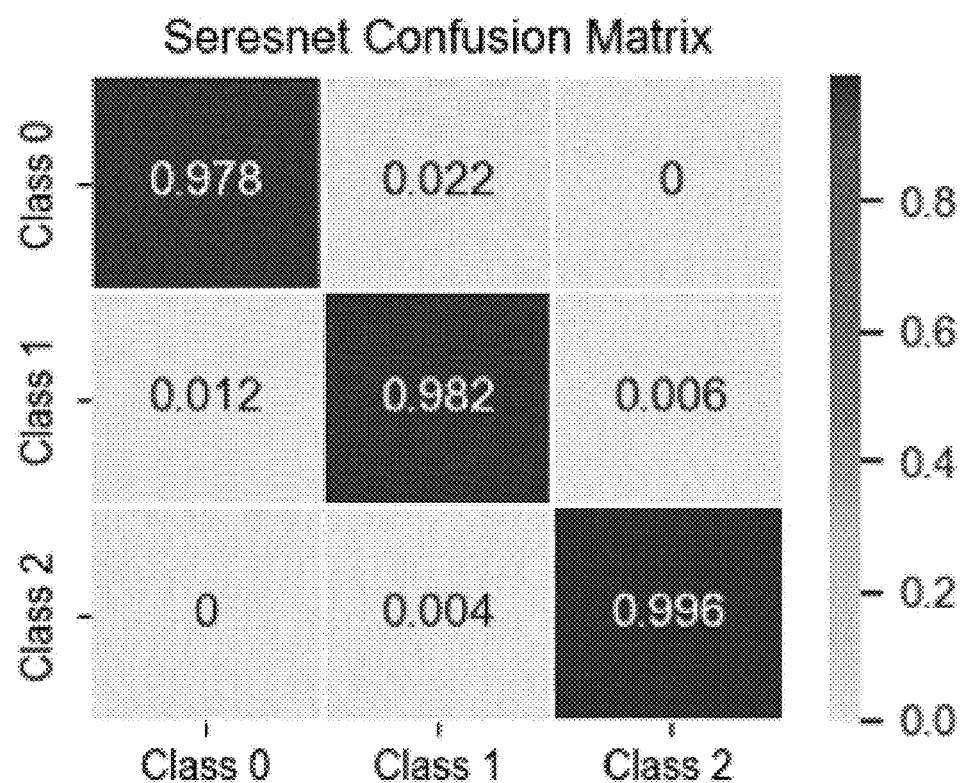
Figure 3E:
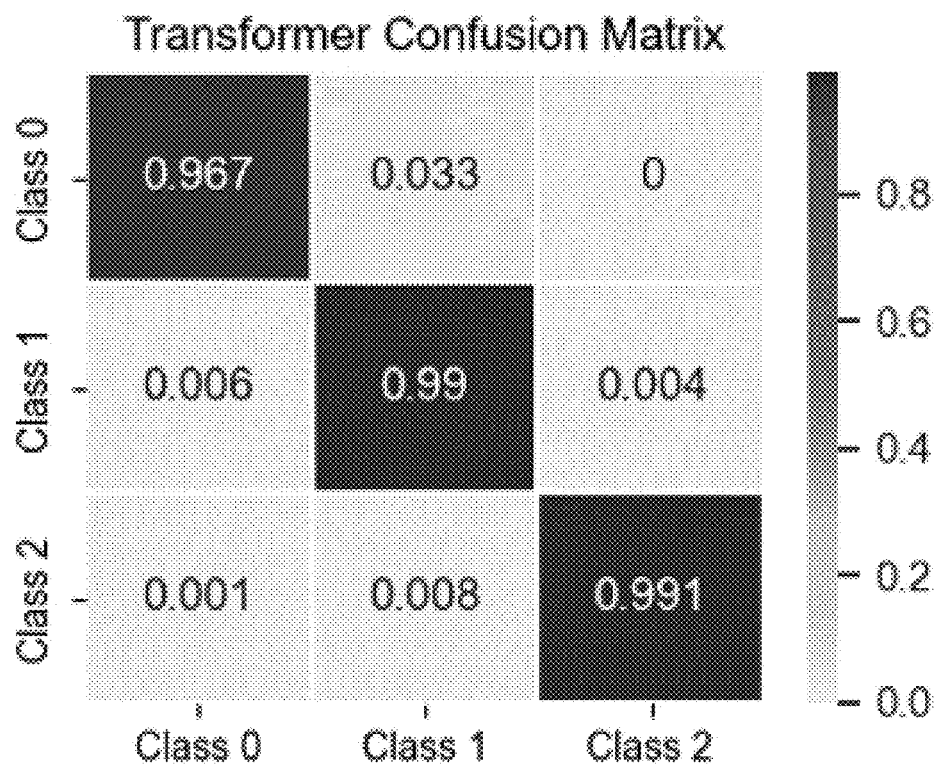
Figure 3F:
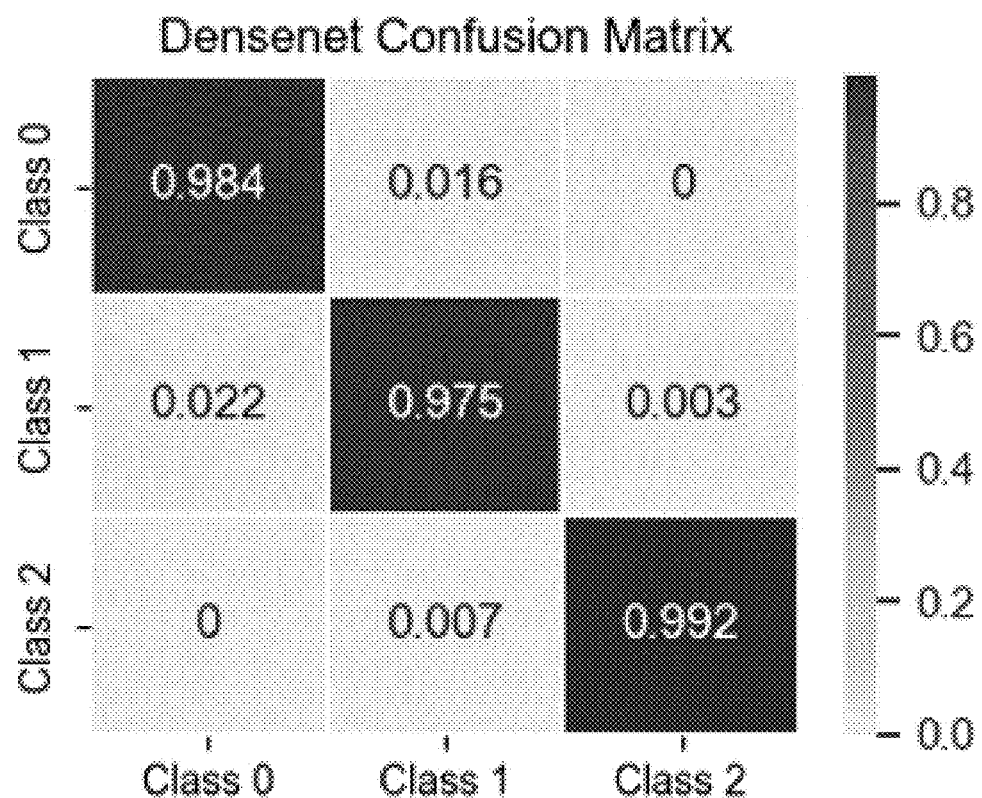

The present disclosure is further described with reference to FIG. 1 and FIGS. 2A-2F.

An ECG signal quality evaluation method based on a multi-scale convolutional and densely connected network includes following steps:

a) n original ECG signals and corresponding labels thereof in a dataset are obtained to obtain original ECG signal set S, where S={$s_1, s_2, \ldots, s_k, \ldots, s_n$}, $s_k$ represents a $k^{th}$ ECG signal, k∈{1, 2, . . . , n}, a corresponding label of the $k^{th}$ ECG signal $s_k$ is $l_k$, an ECG signal label set is L, and L={$l_1, l_2, \ldots, l_k, \ldots, l_n$}.

b) The $k^{th}$ ECG signal $s_k$ is preprocessed to remove a baseline drift and power line interference from the ECG signal $s_k$ to obtain preprocessed ECG signal $x_k$, where a preprocessed ECG signal set is X, and X={$x_1, x_2, \ldots, x_k, \ldots, x_n$}.

c) The preprocessed ECG signal $x_k$ is segmented to obtain i ECG signal fragments {$x_k^1, x_k^2, \ldots, x_k^i$}, where corresponding labels of the i ECG signal fragments {$x_k^1, x_k^2, \ldots, x_k^i$} are {$l_k^1, l_k^2, \ldots l_k^i$}, and a segmented signal fragment set is $X_{seg}$, $X_{seg}$={{$x_1^1, x_1^2, \ldots, x_1^i$}, {$x_2^1, x_2^2, \ldots, x_2^i$}, . . . , {$x_k^1, x_k^2, \ldots, x_k^i$}, . . . , {$x_n^1, x_n^2, \ldots, x_n^i$}}, a segmented signal label set is $L_{seg}$, and $L_{seg}$={{$l_1^1, l_1^2, \ldots, l_1^i$}, {$l_2^1, l_2^2, \ldots, l_2^i$}, . . . , {$l_k^1, l_k^2, \ldots, l_k^i$}, . . . , {$l_n^1, l_n^2, \ldots, l_n^i$}}.

d) Each ECG signal fragment in the signal fragment set $X_{seg}$ is input into a trained AlexNet model to obtain an evaluation-specific ECG signal fragment set $X_{final}$.

e) An improved lightweight densely connected quality classification model is established, and an ECG signal fragment in the evaluation-specific ECG signal fragment set $X_{final}$ is input to the improved lightweight densely connected quality classification model to obtain a classification result.

By combining a deep learning algorithm, the present disclosure proposes an ECG signal quality evaluation method based on a multi-scale convolutional and densely connected network. Firstly, in order to provide more effective interpretative records for subsequent signal analysis, an original ECG signal is preprocessed to remove a baseline drift and power line interference. Then, a trained AlexNet model is used to correct a label of an incorrectly labeled ECG signal fragment after segmentation. Finally, a signal fragment obtained after label correction is input into an improved lightweight densely connected quality classification model to evaluate quality of the ECG signal fragment.

Embodiment 1

The dataset in the step a) is a BUTQDB dataset.

Embodiment 2

In the step b), a high-pass filter with an order of 4 and a cutoff frequency of 0.5 Hz is used to remove the baseline drift from the $k^{th}$ ECG signal $s_k$, and notch filters with cutoff frequencies of 49.1 Hz and 50.6 Hz are used to remove the power line interference from the $k^{th}$ ECG signal $s_k$, to obtain the preprocessed ECG signal $x_k$.

Embodiment 3

In the step c), the preprocessed ECG signal $x_k$ is segmented based on a time length of 1 second to obtain the i ECG signal fragments {$x_k^1, x_k^2, \ldots, x_k^i$}.

Embodiment 4

The step d) includes the following substeps:

d-1) The signal fragment set $X_{seg}$ and the corresponding segmented signal label set $L_{seg}$ are divided into dataset A and dataset B according to a ratio of 1:1. A signal set in the dataset A is $X_{seg\_A}$, a label set in the dataset A is $L_{seg\_A}$, a signal set in the dataset B is $X_{seg\_B}$, and a label set in the dataset B is $L_{seg\_B}$.

d-2) Each ECG signal fragment in the signal set $X_{seg\_A}$ is input into an AlexNet model, and the AlexNet model is trained by using an Adam optimizer based on cross-entropy loss $L_{CE}$ to obtain optimized model AlexNet'$_1$.

d-3) Each ECG signal fragment in the signal set $X_{seg\_B}$ is input into the AlexNet model, and the AlexNet model is trained by using the Adam optimizer based on the cross-entropy loss $L_{CE}$ to obtain optimized model AlexNet''$_2$;

d-4) Each ECG signal fragment in the signal set $X_{seg\_B}$ is input into the optimized model AlexNet'$_1$ to obtain a corrected first label of each ECG signal fragment. If an original label of each ECG signal fragment in the label set $L_{seg\_B}$ is consistent with the first label, or the original label of each ECG signal fragment in the label set $L_{seg\_B}$ is inconsistent with the first label and the first label is greater than confidence coefficient $Con_{thr}$, the ECG signal fragment is retained, where $Con_{thr}=0.9$. If the original label of each ECG signal fragment in the label set $L_{seg\_B}$ is inconsistent with the first label and the first label is less than the confidence coefficient $Con_{thr}$, the ECG signal fragment is discarded, where all retained ECG signal fragments form retained signal fragment set $X'_{seg\_1}$.

d-5) Each ECG signal fragment in the signal set $X_{seg\_A}$ is input into the optimized model AlexNet''$_2$ to obtain a corrected second label of each ECG signal fragment. If an original label of each ECG signal fragment in the label set $L_{seg\_A}$ is consistent with the second label, or the original label of each ECG signal fragment in the label set $L_{seg\_A}$ is inconsistent with the second label and the second label is greater than the confidence coefficient $Con_{thr}$, the ECG signal fragment is retained. If the original label of each ECG signal fragment in the label set $L_{seg\_A}$ is inconsistent with the second label and the second label is less than the confidence coefficient $Con_{thr}$, the ECG signal fragment is discarded, where all retained ECG signal fragments form retained signal fragment set $X''_{seg\_1}$.

d-6) The final quality evaluation-specific ECG signal fragment set $X_{final}$ is calculated according to formula $X_{final}=X'_{seg\_1}+X''_{seg\_2}$.

Embodiment 5

In the step d-2), a batch size is set to 512 when the AlexNet model is trained by using the Adam optimizer based on the cross-entropy loss $L_{CE}$. In the step d-3), the batch size is set to 512 when the AlexNet model is trained by using the Adam optimizer based on the cross-entropy loss $L_{CE}$.

Embodiment 6

The step e) includes the following substeps:

e-1) The improved lightweight densely connected quality classification model is constituted by a feature extraction module and a classification module. The feature extraction module is constituted by first multi-scale channel attention module $MCA_1$, second multi-scale channel attention module $MCA_2$, third multi-scale channel attention module $MCA_3$, first multi-scale feature densely connected module $MFD_1$, second multi-scale feature densely connected module $MFD_2$, and third multi-scale feature densely connected module $MFD_3$. The classification module is constituted by a linear layer.

e-2) The first multi-scale channel attention module $MCA_1$ is constituted by a first convolution unit, a second convolution unit, a third convolution unit, an SE attention module, and an average pooling layer. The first convolution unit is sequentially constituted by a convolutional layer, a BN layer, and a Relu activation function layer. The second convolution unit is sequentially constituted by a convolutional layer, a BN layer, and a Relu activation function layer. The third convolution unit is sequentially constituted by a convolutional layer, a BN layer, and a Relu activation function layer. The ECG signal fragment in the evaluation-specific ECG signal fragment set $X_{final}$ is input into the first convolution unit to obtain shallow feature signal $X_{mca1}\_f_0$. The ECG signal fragment in the evaluation-specific ECG signal fragment set $X_{final}$ is input into the second convolution unit to obtain shallow feature signal $X_{mca1}\_f_1$. The ECG signal fragment in the evaluation-specific ECG signal fragment set $X_{final}$ is input into the third convolution unit to obtain shallow feature signal $X_{mca1}\_f_2$. The shallow feature signal $X_{mca1}\_f_0$, the shallow feature signal $X_{mca1}\_f_1$, and the shallow feature signal $X_{mca1}\_f_2$ are concatenated to obtain feature signal $X_{mca1}\_f_3$. The feature signal $X_{mca1}\_f_3$ is input into the SE attention module to obtain important feature information $X_{mca1}\_f_{se}$. The important feature information $X_{mca1}\_f_{se}$ is input into the average pooling layer for downsampling to obtain feature signal $X_{mca1}\_f_4$.

e-3) The first multi-scale feature densely connected module $MFD_1$ is constituted by a first densely connected layer, a second densely connected layer, a third densely connected layer, a fourth densely connected layer, a fifth densely connected layer, and a sixth densely connected layer. The first densely connected layer, the second densely connected layer, the third densely connected layer, the fourth densely connected layer, the fifth densely connected layer, and the sixth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer. The feature signal $X_{mca1}\_f_4$ is input into the first densely connected layer to obtain feature signal $X_{mfd1}\_f_1$. The feature signal $X_{mca1}\_f_4$ and the feature signal $X_{mfd1}\_f_1$ are concatenated, and then a concatenated signal is input into the second densely connected layer to obtain feature signal $X_{mfd1}\_f_2$. The feature signal $X_{mca1}\_f_4$, the feature signal $X_{mfd1}\_f_1$, and the feature signal $X_{mfd1}\_f_2$ are concatenated, and then a concatenated signal is input into the third densely connected layer to obtain feature signal $X_{mfd1}\_f_3$. The feature signal $X_{mca1}\_f_4$, the feature signal $X_{mfd1}\_f_1$, the feature signal $X_{mfd1}\_f_2$, and the feature signal $X_{mfd1}\_f_3$ are concatenated, and then a concatenated signal is input into the fourth densely connected layer to obtain feature signal $X_{mfd1}\_f_4$. The feature signal $X_{mca1}\_f_4$, the feature signal $X_{mfd1}\_f_1$, the feature signal $X_{mfd1}\_f_2$, the feature signal $X_{mfd1}\_f_3$, and the feature signal $X_{mfd1}\_f_4$ are concatenated, and then a concatenated signal is input into the fifth densely connected layer to obtain feature signal $X_{mfd1}\_f_5$. The feature signal $X_{mca1}\_f_4$, the feature signal $X_{mfd1}\_f_1$, the feature signal $X_{mfd1}\_f_2$, the feature signal $X_{mfd1}\_f_3$, the feature signal $X_{mfd1}\_f_4$, and the feature signal $X_{mfd1}\_f_5$ are concatenated, and then a concatenated signal is input into the sixth densely connected layer to obtain feature signal $X_{mfd1}\_f_6$. After a feature weight of the ECG signal is calibrated through the sigmoid activation function layer, an important waveform feature can be extracted.

e-4) The second multi-scale channel attention module $MCA_2$ is constituted by a first convolution unit, a second convolution unit, a third convolution unit, an SE attention module, and an average pooling layer. The first convolution unit is sequentially constituted by a convolutional layer, a BN layer, and a Relu activation function layer. The second convolution unit is sequentially constituted by a convolutional layer, a BN layer, and a Relu activation function layer. The third convolution unit is sequentially constituted by a convolutional layer, a BN layer, and a Relu activation function layer. The feature signal $X_{mfd1}\_f_6$ is input into the first convolution unit to obtain shallow feature signal $X_{mca2}\_f_0$. The feature signal $X_{mfd1}\_f_6$ is input into the second convolution unit to obtain shallow feature signal $X_{mca2}\_f_1$. The feature signal $X_{mfd1}\_f_6$ is input into the third convolution unit to obtain shallow feature signal $X_{mca2}\_f_2$. The shallow feature signal $X_{mca2}\_f_0$, the shallow feature signal $X_{mca2}\_f_1$, and the shallow feature signal $X_{mca2}\_f_2$ are concatenated to obtain feature signal $X_{mca2}\_f_3$. The feature signal $X_{mca2}\_f_3$ is input into the SE attention module to obtain important feature information $X_{mca2}\_f_{se}$. The important feature information $X_{mca2}\_f_{se}$ is input into the average pooling layer for downsampling to obtain feature signal $X_{mca2}\_f_4$.

e-5) The second multi-scale feature densely connected module $MFD_2$ is constituted by a first densely connected layer, a second densely connected layer, a third densely connected layer, and a fourth densely connected layer. The first densely connected layer, the second densely connected layer, the third densely connected layer, and the fourth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer. The feature signal $X_{mca2}\_f_4$ is input into the first densely connected layer to obtain feature signal $X'_{mfd2}\_f_1$. The feature signal $X_{mca2}\_f_4$ and the feature signal $X'_{mfd2}\_f_1$ are concatenated, and then a concatenated signal is input into the second densely connected layer to obtain feature signal $X'_{mfd2}\_f_2$. The feature signal $X_{mca2}\_f_4$, the feature signal $X'_{mfd2}\_f_1$, and the feature signal $X'_{mfd2}\_f_2$ are concatenated, and then a concatenated signal is input into the third densely connected layer to obtain feature signal $X'_{mfd2}\_f_3$. The feature signal $X_{mca2}\_f_4$, the feature signal $X'_{mfd2}\_f_1$, the feature signal $X'_{mfd2}\_f_2$, and the feature signal $X'_{mfd2}\_f_3$ are concatenated, and then a concatenated signal is input into the fourth densely connected layer to obtain feature signal $X'_{mfd2}\_f_4$. After the feature weight of the ECG signal is calibrated through the sigmoid activation function layer, the important waveform feature can be extracted.

e-6) The third multi-scale channel attention module $MCA_3$ is constituted by a first convolution unit, a second convolution unit, a third convolution unit, an SE attention module, and an average pooling layer. The first convolution unit is sequentially constituted by a convolutional layer, a BN layer, and a Relu activation function layer. The second convolution unit is sequentially constituted by a convolutional layer, a BN layer, and a Relu activation function layer. The third convolution unit is sequentially constituted by a convolutional layer, a BN layer, and a Relu activation function layer. The feature signal $X'_{mfd2}\_f_4$ is input into the first convolution unit to obtain shallow feature signal $X_{mca3}\_f_0$. The feature signal $X'_{mfd2}\_f_4$ is input into the second convolution unit to obtain shallow feature signal $X_{mca3}\_f_1$. The feature signal $X'_{mfd2}\_f_4$ is input into the third convolution unit to obtain shallow feature signal $X_{mca3}\_f_2$. The shallow feature signal $X_{mca3}\_f_0$, the shallow feature signal $X'_{mfd3}\_f_1$, and the shallow feature signal $X_{mca3}\_f_2$ are concatenated to obtain feature signal $X_{mca3}\_f_3$. The feature signal $X_{mca3}\_f_3$ is input into the SE attention module to obtain important feature information $X_{mca3}\_f_{se}$. The important feature information $X_{mca3}\_f_{se}$ is input into the average pooling layer for downsampling to obtain feature signal $X_{mca3}\_f_4$.

e-7) The third multi-scale feature densely connected module $MFD_3$ is constituted by a first densely connected layer, a second densely connected layer, a third densely connected layer, and a fourth densely connected layer. The first densely connected layer, the second densely connected layer, the third densely connected layer, and the fourth densely connected layer each are sequentially constituted by a first BN layer, a first Relu activation function layer, a first dilated convolutional layer, a second BN layer, a second Relu activation function layer, a multi-scale convolutional layer, and a sigmoid activation function layer. The feature signal $X_{mca3}\_f_4$ is input into the first densely connected layer to obtain feature signal $X''_{mfd3}\_f_1$. The feature signal $X_{mca3}\_f_4$ and the feature signal $X''_{mfd3}\_f_1$ are concatenated, and then a concatenated signal is input into the second densely connected layer to obtain feature signal $X''_{mfd3}\_f_2$. The feature signal $X_{mca3}\_f_4$, the feature signal $X''_{mfd3}\_f_1$, and the feature signal $X''_{mfd3}\_f_2$ are concatenated, and then a concatenated signal is input into the third densely connected layer to obtain feature signal $X''_{mfd3}\_f_3$. The feature signal $X_{mca3}\_f_4$, the feature signal $X''_{mfd3}\_f_1$, the feature signal $X''_{mfd3}\_f_2$, and the feature signal $X''_{mfd3}\_f_3$ are concatenated, and then a concatenated signal is input into the fourth densely connected layer to obtain feature signal $X''_{mfd3}\_f_4$. After the feature weight of the ECG signal is calibrated through the sigmoid activation function layer, the important waveform feature can be extracted.

e-8) The feature signal $X''_{mfd3}\_f_4$ is input into the classification module of the improved lightweight densely connected quality classification model to obtain the classification result, and a quantity of output neurons in the linear layer is set to 3 (the quantity of neurons is a quantity of categories).

In this embodiment, preferably, in the step e-2), the convolutional layer of the first convolution unit has a 1×7 convolution kernel, a step of 3, and 16 channels, the convolutional layer of the second convolution unit has a 1×5 convolution kernel, a step of 3, and 16 channels, the convolutional layer of the third convolution unit has a 1×3 convolution kernel, a step of 3, and 16 channels, and the average pooling layer has a 1×2 pooling kernel and a step of 2. In the step e-3), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3; the third dilated convolutional layer has a 1×5 convolution kernel, 8 channels, a dilation rate of 2, and a step of 3, with a padding of 1; and the fourth dilated convolutional layer has a 1×7 convolution kernel, 8 channels, a dilation rate of 4, and a step of 3, with a padding of 1. In the step e-4), the convolutional layer of the first convolution unit has a 1×7 convolution kernel, a step of 3, and 32 channels, the convolutional layer of the second convolution unit has a 1×5 convolution kernel, a step of 3, and 32 channels, the convolutional layer of the third convolution unit has a 1×3 convolution kernel, a step of 3, and 32 channels, and the average pooling layer has a 1×2 pooling kernel and a step of 2. In the step e-5), the first dilated convolutional layer has a 1×1 convolution kernel, 16 channels, a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3, the third dilated convolutional layer has a 1×5 convolution kernel, 8 channels, a dilation rate of 2, and a step of 3, with a padding of 1, and the fourth dilated convolutional layer has a 1×7 convolution kernel, 8 channels, a dilation rate of 4, and a step of 3, with a padding of 1. In the step e-6), the convolutional layer of the first convolution unit has a 1×7 convolution kernel, a step of 3, and 64 channels, the convolutional layer of the second convolution unit has a 1×5 convolution kernel, a step of 3, and 64 channels, the convolutional layer of the third convolution unit has a 1×3 convolution kernel, a step of 3, and 64 channels, and the average pooling layer has a 1×2 pooling kernel and a step of 2. In the step e-7), the first dilated convolutional layer has a 1×1 convolution kernel, 16 channels, a dilation rate of 2, and the multi-scale convolutional layer is sequentially constituted by a second dilated convolutional layer, a third dilated convolutional layer, and a fourth dilated convolutional layer, where the second dilated convolutional layer has a 1×3 convolution kernel, 8 channels, a dilation rate of 1, and a step of 3, the third dilated convolutional layer has a 1×5 convolution kernel, 8 channels, a dilation rate of 2, and a step of 3, with a padding of 1, and the fourth dilated convolutional layer has a 1×7 convolution kernel, 8 channels, a dilation rate of 4, and a step of 3, with a padding of 1.

Embodiment 7

The ECG signal quality evaluation method based on a multi-scale convolutional and densely connected network further includes: after the step e), training the improved lightweight densely connected quality classification model by using a cross-entropy loss function and a backpropagation algorithm.

Taking data in public dataset BUTQDB as an example, the following specifically describes implementations of the present disclosure.

ECG signal data and corresponding labels are obtained from the BUTQDB dataset to construct an improved lightweight densely connected quality classification model. The model is constituted by feature extraction modules (first multi-scale channel attention module $MCA_1$, second multi-scale channel attention module $MCA_2$, third multi-scale channel attention module $MCA_3$, first multi-scale feature densely connected module $MFD_1$, second multi-scale feature densely connected module $MFD_2$, and third multi-scale feature densely connected module $MFD_3$). A classification module is constituted by a linear layer. An ECG signal in the BUTQDB dataset is preprocessed to remove a baseline drift and power line interference. A preprocessed ECG signal is segmented into 1-second ECG signal fragments, and a corresponding label of each ECG signal fragment is obtained. Inspired by the "co-training" method, a one-dimensional AlexNet model is used to mutually re-label the ECG signal fragment based on consistency and confidence coefficient (0.9) principles. FIGS. 2A-2F show changes of six randomly selected signal labels before and after the re-labeling (0 represents good quality, 1 represents medium quality, and 2 represents poor quality). Based on FIGS. 2A-2F, it can be intuitively seen that quality of the signal is more consistent with a class after the re-labeling, which means it is necessary to carry out label re-labeling.

The model proposed in the present disclosure is compared with mainstream classification task models (Resnet, Seresnet, and Transformer) and currently proposed lightweight models (MobileNetXt and ShuffleNet-v2). A unified experimental condition is adopted for all the models that need to be compared. Accuracy, sensitivity, precision, an F1 score, a model parameter quantity (Params), and floating-point operations (FLOPs) are selected as evaluation indicators.

The BUTQDB dataset is used for training and testing. FIGS. 3A-3F show results of comparing confusion matrices for different models. An experimental result is shown in Table 1.

TABLE 1

Result of comparing models in a BUTQDB dataset

| Network | Accuracy (%) | Sensitivity (%) | Precision (%) | F1 Score (%) |
|---|---|---|---|---|
| MobileNetXt | 97.85 | 98.13 | 97.79 | 97.96 |
| ShuffleNet-v2 | 97.64 | 98.03 | 97.51 | 97.77 |
| Resnet | 98.00 | 98.17 | 97.96 | 98.06 |
| Seresnet | 98.21 | 98.53 | 98.14 | 98.33 |
| Transformer | 97.80 | 98.25 | 97.75 | 97.98 |
| Ours | 98.23 | 98.37 | 98.34 | 98.35 |

Based on the statistical data, it can be included that the model proposed in the present disclosure achieves same classification performance as the mainstream classification model Seresnet, but has higher accuracy, higher precision, and a higher F1 score compared with all other models, especially compared with the proposed lightweight model. This means that the model proposed in the present disclosure has better overall performance and a lower missed diagnosis rate in an evaluation process, and can provide more acceptable signals for subsequent tasks. In summary, from a perspective of model performance, the model proposed in the present disclosure has a good capability to distinguish between acceptable and unacceptable ECG signals in an actual environment.

Figure 4A:
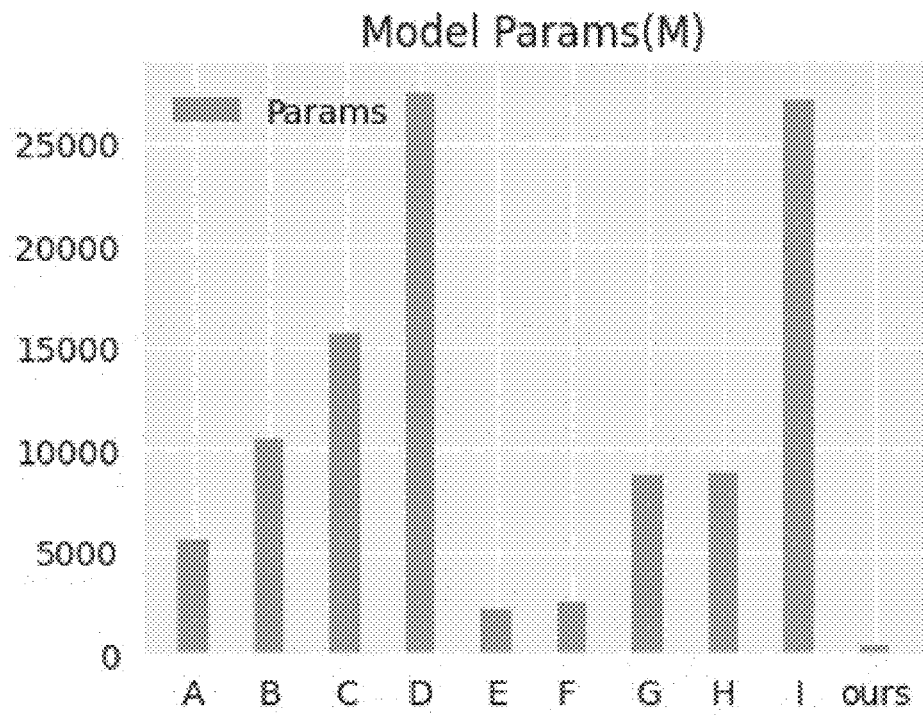
FIGS. 4A-4B compare parameter quantities and floating-point operations for different models.
Figure 4B:
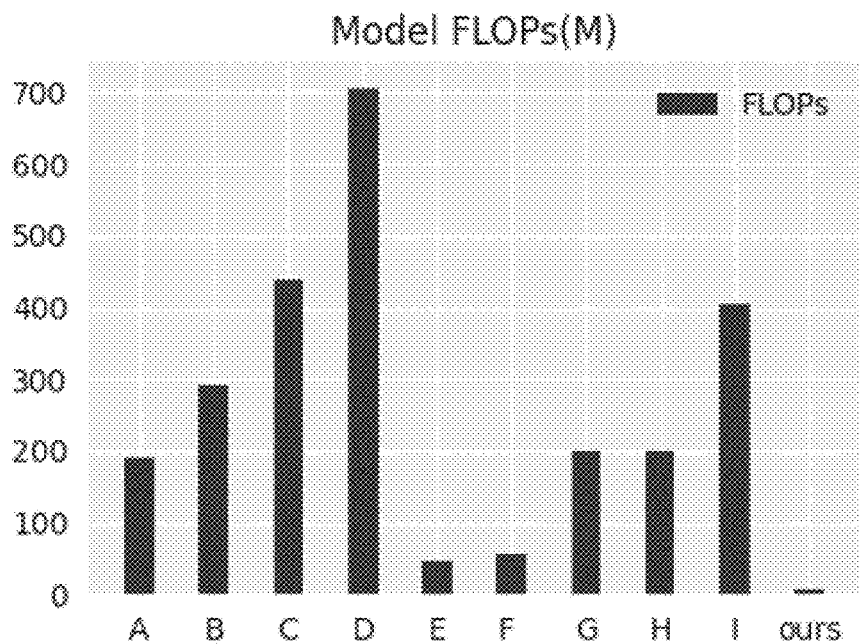

FIGS. 4A-4B show results of comparing the model proposed in the present disclosure with baseline models (DenseNet-121 (A), DenseNet-169 (B), DenseNet-201 (C), and DenseNet-264 (D)), mainstream classification task models (Resnet (G), Seresnet (H), and Transformer (I)), and currently proposed lightweight models (MobileNetXt (E) and ShuffleNet v2 (F)) in terms of the parameter quantity and the floating-point operations. From FIGS. 4A-4B, it can be intuitively seen that parameter quantities and computation amounts of other models are 40 to 500 times those of the model proposed in the present disclosure. This indicates that compared with the baseline model DenseNet and other neural network models, the model proposed in the present disclosure can achieve relatively good performance with least parameters and floating-point operations.

What is claimed is:

1. An electrocardiograph (ECG) signal quality evaluation method based on a multi-scale convolutional and densely connected network, comprising:
   a) obtaining n original ECG signals and corresponding labels of the n original ECG signals in a dataset to obtain an original ECG signal set S, wherein S={$s_1$, $s_2$, ..., $s_k$, ..., $s_n$}, $s_k$ represents a $k^{th}$ ECG signal, k∈{1, 2, ..., n}, a corresponding label of the $k^{th}$ ECG signal $s_k$ is $l_k$, an ECG signal label set is L, and L={$l_1$, $l_2$, ..., $l_k$, ..., $l_n$};

b) preprocessing the $k^{th}$ ECG signal $s_k$ to remove a baseline drift and power line interference from the ECG signal $s_k$ to obtain a preprocessed ECG signal $x_k$, wherein a preprocessed ECG signal set is X, and $X=\{x_1, x_2, \ldots, x_k, \ldots, x_n\}$;

c) segmenting the preprocessed ECG signal $x_k$ to obtain i ECG signal fragments $\{x_k^1, x_k^2, \ldots, x_k^i\}$, wherein corresponding labels of the i ECG signal fragments $\{x_k^1, x_k^2, \ldots, x_k^i\}$ are $\{l_k^1, l_k^2, \ldots l_k^i\}$, and a segmented signal fragment set is $X_{seg}$, $X_{seg}=\{\{x_1^1, x_1^2, \ldots, x_1^i\}, \{x_2^1, x_2^2, \ldots, x_2^i\}, \ldots, \{x_k^1, x_k^2, \ldots, x_k^i\}, \ldots, \{x_n^1, x_n^2, \ldots, x_n^i\}\}$, a segmented signal label set is $L_{seg}$, and $L_{seg}=\{\{l_1^1, l_1^2, \ldots, l_1^i\}, \{l_2^1, l_2^2, \ldots, l_2^i\}, \ldots, \{l_k^1, l_k^2, \ldots, l_k^i\}, \ldots, \{l_n^1, l_n^2, \ldots, l_n^i\}\}$;

d) inputting each ECG signal fragment in the signal fragment set $X_{seg}$ into a trained AlexNet model to obtain an evaluation-specific ECG signal fragment set $X_{final}$; and e) establishing an improved lightweight densely connected quality classification model, and inputting an ECG signal fragment in the evaluation-specific ECG signal fragment set $X_{final}$ into the improved lightweight densely connected quality classification model to obtain a classification result;

wherein the step e) comprises the following substeps:

e-1) constituting the improved lightweight densely connected quality classification model by a feature extraction module and a classification module, wherein the feature extraction module is constituted by a first multi-scale channel attention module $MCA_1$, a second multi-scale channel attention module $MCA_2$, a third multi-scale channel attention module $MCA_3$, a first multi-scale feature densely connected module $MFD_1$, a second multi-scale feature densely connected module $MFD_2$, and a third multi-scale feature densely connected module $MFD_3$, and the classification module is constituted by a linear layer;

e-2) constituting the first multi-scale channel attention module $MCA_1$ by a first convolution unit, a second convolution unit, a third convolution unit, a squeeze-and-excitation (SE) attention module, and an average pooling layer, wherein the first convolution unit is sequentially constituted by a convolutional layer, a batch normalization (BN) layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer;

inputting the ECG signal fragment in the evaluation-specific ECG signal fragment set $X_{final}$ into the first convolution unit to obtain a shallow feature signal $X_{mca1}\_f_0$;

inputting the ECG signal fragment in the evaluation-specific ECG signal fragment set $X_{final}$ into the second convolution unit to obtain a shallow feature signal $X_{mca1}\_f_1$;

inputting the ECG signal fragment in the evaluation-specific ECG signal fragment set $X_{final}$ into the third convolution unit to obtain a shallow feature signal $X_{mca1}\_f_2$;

concatenating the shallow feature signal $X_{mca1}\_f_0$, the shallow feature signal $X_{mca1}\_f_1$, and the shallow feature signal $X_{mca1}\_f_2$ to obtain a feature signal $X_{mca1}\_f_3$;

inputting the feature signal $X_{mca1}\_f_3$ into the SE attention module to obtain important feature information $X_{mca1}\_f_{se}$; and inputting the important feature information $X_{mca1}\_f_{se}$ into the average pooling layer to obtain a feature signal $X_{mca1}\_f_4$;

e-3) constituting the first multi-scale feature densely connected module $MFD_1$ by a first densely connected layer, a second densely connected layer, a third densely connected layer, a fourth densely connected layer, a fifth densely connected layer, and a sixth densely connected layer, wherein the first densely connected layer, the second densely connected layer, the third densely connected layer, the fourth densely connected layer, the fifth densely connected layer, and the sixth densely connected layer each are sequentially constituted by a first BN layer, a first Relu activation function layer, a first dilated convolutional layer, a first sigmoid activation function layer, a second BN layer, a second Relu activation function layer, a multi-scale convolutional layer, and a second sigmoid activation function layer;

inputting the feature signal $X_{mca1}\_f_4$ into the first densely connected layer to obtain a feature signal $X_{mfd1}\_f_1$;

concatenating the feature signal $X_{mca1}\_f_4$ and the feature signal $X_{mfd1}\_f_1$ to obtain a first concatenated signal, and inputting the first concatenated signal into the second densely connected layer to obtain a feature signal $X_{mfd1}\_f_2$;

concatenating the feature signal $X_{mca1}\_f_4$, the feature signal $X_{mfd1}\_f_1$, and the feature signal $X_{mfd1}\_f_2$ to obtain a second concatenated signal, and inputting the second concatenated signal into the third densely connected layer to obtain a feature signal $X_{mfd1}\_f_3$;

concatenating the feature signal $X_{mca1}\_f_4$, the feature signal $X_{mfd1}\_f_1$, the feature signal $X_{mfd1}\_f_2$, and the feature signal $X_{mfd1}\_f_3$ to obtain a third concatenated signal, and inputting the third concatenated signal into the fourth densely connected layer to obtain a feature signal $X_{mfd1}\_f_4$;

concatenating the feature signal $X_{mca1}\_f_4$, the feature signal $X_{mfd1}\_f_1$, the feature signal $X_{mfd1}\_f_2$, the feature signal $X_{mfd1}\_f_3$, and the feature signal $X_{mfd1}\_f_4$ to obtain a fourth concatenated signal, and inputting the fourth concatenated signal into the fifth densely connected layer to obtain a feature signal $X_{mfd1}\_f_5$; and concatenating the feature signal $X_{mca1}\_f_4$, the feature signal $X_{mfd1}\_f_1$, the feature signal $X_{mfd1}\_f_2$, the feature signal $X_{mfd1}\_f_3$, the feature signal $X_{mfd1}\_f_4$, and the feature signal $X_{mfd1}\_f_5$ to obtain a fifth concatenated signal, and inputting the fifth concatenated signal into the sixth densely connected layer to obtain a feature signal $X_{mfd1}\_f_6$;

e-4) constituting the second multi-scale channel attention module $MCA_2$ by a first convolution unit, a second convolution unit, a third convolution unit, an SE attention module, and an average pooling layer, wherein the first convolution unit is sequentially constituted by a convolutional layer, a BN layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer;

inputting the feature signal $X_{mfd1}\_f_6$ into the first convolution unit to obtain a shallow feature signal $X_{mca2}\_f_0$;

inputting the feature signal $X_{mfd1}\_f_6$ into the second convolution unit to obtain a shallow feature signal $X_{mca2}\_f_1$;

inputting the feature signal $X_{mfd1}\_f_6$ into the third convolution unit to obtain a shallow feature signal $X_{mca2}\_f_2$;

concatenating the shallow feature signal $X_{mca2}\_f_0$, the shallow feature signal $X_{mca2}\_f_1$, and the shallow feature signal $X_{mca2}\_f_2$ to obtain a feature signal $X_{mca2}\_f_3$;

inputting the feature signal $X_{mca2}\_f_3$ into the SE attention module to obtain important feature information $X_{mca2}\_f_{se}$; and inputting the important feature information $X_{mca2}\_f_{se}$ into the average pooling layer to obtain a feature signal $X_{mca2}\_f_4$;

e-5) constituting the second multi-scale feature densely connected module $MFD_2$ by a first densely connected layer, a second densely connected layer, a third densely connected layer, and a fourth densely connected layer, wherein the first densely connected layer, the second densely connected layer, the third densely connected layer, and the fourth densely connected layer each are sequentially constituted by a first BN layer, a first Relu activation function layer, a first dilated convolutional layer, a first sigmoid activation function layer, a second BN layer, a second Relu activation function layer, a multi-scale convolutional layer, and a second sigmoid activation function layer;

inputting the feature signal $X_{mca2}\_f_4$ into the first densely connected layer to obtain a feature signal $X'_{mfd2}\_f_1$;

concatenating the feature signal $X_{mca2}\_f_4$ and the feature signal $X'_{mfd2}\_f_1$ to obtain a sixth concatenated signal, and inputting the sixth concatenated signal into the second densely connected layer to obtain a feature signal $X'_{mfd2}\_f_2$;

concatenating the feature signal $X_{mca2}\_f_4$, the feature signal $X'_{mfd2}\_f_1$, and the feature signal $X'_{mfd2}\_f_2$ to obtain a seventh concatenated signal, and inputting the seventh concatenated signal into the third densely connected layer to obtain a feature signal $X'_{mfd2}\_f_3$; and concatenating the feature signal $X_{mca2}\_f_4$, the feature signal $X'_{mfd2}\_f_1$, the feature signal $X'_{mfd2}\_f_2$, and the feature signal $X'_{mfd2}\_f_3$ to obtain an eighth concatenated signal, and inputting the eighth concatenated signal into the fourth densely connected layer to obtain a feature signal $X'_{mfd2}\_f_4$;

e-6) constituting the third multi-scale channel attention module $MCA_3$ by a first convolution unit, a second convolution unit, a third convolution unit, an SE attention module, and an average pooling layer, wherein the first convolution unit is sequentially constituted by a convolutional layer, a BN layer, and a Relu activation function layer, the second convolution unit is sequentially constituted by a convolutional layer, a BN layer, and a Relu activation function layer, the third convolution unit is sequentially constituted by a convolutional layer, a BN layer, and a Relu activation function layer;

inputting the feature signal $X'_{mfd2}\_f_4$ into the first convolution unit to obtain a shallow feature signal $X_{mca3}\_f_0$;

inputting the feature signal $X'_{mfd2}\_f_4$ into the second convolution unit to obtain a shallow feature signal $X_{mca3}\_f_1$;

inputting the feature signal $X'_{mfd2}\_f_4$ into the third convolution unit to obtain a shallow feature signal $X_{mca3}\_f_2$;

concatenating the shallow feature signal $X_{mca3}\_f_0$, the shallow feature signal $X_{mca3}\_f_1$, and the shallow feature signal $X_{mca3}\_f_2$ to obtain a feature signal $X_{mca3}\_f_3$;

inputting the feature signal $X_{mca3}\_f_3$ into the SE attention module to obtain important feature information $X_{mca3}\_f_{se}$; and inputting the important feature information $X_{mca3}\_f_{se}$ into the average pooling layer to obtain a feature signal $X_{mca3}\_f_4$;

e-7) constituting the third multi-scale feature densely connected module $MED_3$ by a first densely connected layer, a second densely connected layer, a third densely connected layer, and a fourth densely connected layer, wherein the first densely connected layer, the second densely connected layer, the third densely connected layer, and the fourth densely connected layer each are sequentially constituted by a first BN layer, a first Relu activation function layer, a first dilated convolutional layer, a first sigmoid activation function layer, a second BN layer, a second Relu activation function layer, a multi-scale convolutional layer, and a second sigmoid activation function layer;

inputting the feature signal $X_{mca3}\_f_4$ into the first densely connected layer to obtain a feature signal $X''_{mfd3}\_f_1$;

concatenating the feature signal $X_{mca3}\_f_4$ and the feature signal $X''_{mfd3}\_f_1$ to obtain a ninth concatenated signal, and inputting the ninth concatenated signal into the second densely connected layer to obtain a feature signal $X''_{mfd3}\_f_2$;

concatenating the feature signal $X_{mca3}\_f_4$, the feature signal $X''_{mfd3}\_f_1$, and the feature signal $X''_{mfd3}\_f_2$ to obtain a tenth concatenated signal, and inputting the tenth concatenated signal into the third densely connected layer to obtain a feature signal $X''_{mfd3}\_f_3$; and concatenating the feature signal $X_{mca3}\_f_4$, the feature signal $X''_{mfd3}\_f_1$, the feature signal $X''_{mfd3}\_f_2$, and the feature signal $X''_{mfd3}\_f_3$ to obtain an eleventh concatenated signal, and inputting the eleventh concatenated signal into the fourth densely connected layer to obtain a feature signal $X''_{mfd3}\_f_4$; and e-8) inputting the feature signal $X''_{mfd3}\_f_4$ into the classification module of the improved lightweight densely connected quality classification model to obtain the classification result, and setting a quantity of output neurons in the linear layer to 3.

2. The ECG signal quality evaluation method based on the multi-scale convolutional and densely connected network according to claim 1, wherein the dataset in the step a) is a Brno University of Technology ECG Quality Database (BUTQDB) dataset.

3. The ECG signal quality evaluation method based on the multi-scale convolutional and densely connected network according to claim 1, wherein in the step b), a high-pass filter with an order of 4 and a cutoff frequency of 0.5 Hz is configured to remove the baseline drift from the $k^{th}$ ECG signal $S_k$, and notch filters with cutoff frequencies of 49.1 Hz and 50.6 Hz are configured to remove the power line interference from the $k^{th}$ ECG signal $S_k$, to obtain the preprocessed ECG signal $x_k$.

4. The ECG signal quality evaluation method based on the multi-scale convolutional and densely connected network according to claim 1, wherein in the step c), the preprocessed ECG signal $X_k$ is segmented based on a time length of 1 second to obtain the i ECG signal fragments $\{x_k^1, x_k^2, \ldots, x_k^i\}$.

5. The ECG signal quality evaluation method based on the multi-scale convolutional and densely connected network according to claim 1, wherein the step d) comprises the following substeps:

d-1) dividing the signal fragment set $X_{seg}$ and the corresponding segmented signal label set $L_{seg}$ into a dataset A and a dataset B according to a ratio of 1:1, wherein a signal set in the dataset A is $X_{seg\_A}$, a label set in the dataset A is $L_{seg\_A}$, a signal set in the dataset B is $X_{seg\_B}$, and a label set in the dataset B is $L_{seg\_B}$;

d-2) inputting each ECG signal fragment in the signal set $X_{seg\_A}$ into an AlexNet model, and training the AlexNet model by using an Adam optimizer based on a cross-entropy loss $L_{CE}$ to obtain an optimized model AlexNet'$_1$;

d-3) inputting each ECG signal fragment in the signal set $X_{seg\_B}$ into the AlexNet model, and training the AlexNet model by using the Adam optimizer based on the cross-entropy loss $L_{CE}$ to obtain an optimized model AlexNet"$_2$;

d-4) inputting each ECG signal fragment in the signal set $X_{seg\_B}$ into the optimized model AlexNet'$_1$ to obtain a corrected first label of each ECG signal fragment; and if an original label of each ECG signal fragment in the label set $L_{seg\_B}$ is consistent with the first label, or the original label of each ECG signal fragment in the label set $L_{seg\_B}$ is inconsistent with the first label and the first label is greater than a confidence coefficient $Con_{thr}$, retaining the ECG signal fragment, wherein $Con_{thr}=0.9$; or if the original label of each ECG signal fragment in the label set $L_{seg\_B}$ is inconsistent with the first label and the first label is less than the confidence coefficient $Con_{thr}$, discarding the ECG signal fragment, wherein all retained ECG signal fragments form a retained signal fragment set $X'_{seg\_1}$;

d-5) inputting each ECG signal fragment in the signal set $X_{seg\_A}$ into the optimized model AlexNet"$_2$ to obtain a corrected second label of each ECG signal fragment; and if an original label of each ECG signal fragment in the label set $L_{seg\_A}$ is consistent with the second label, or the original label of each ECG signal fragment in the label set $L_{seg\_A}$ is inconsistent with the second label and the second label is greater than the confidence coefficient $Con_{thr}$, retaining the ECG signal fragment; or if the original label of each ECG signal fragment in the label set $L_{seg\_A}$ is inconsistent with the second label and the second label is less than the confidence coefficient $Con_{thr}$, discarding the ECG signal fragment, wherein all retained ECG signal fragments form a retained signal fragment set $X''_{seg\_2}$; and d-6) calculating the final quality evaluation-specific ECG signal fragment set $X_{final}$ according to a formula $X_{final}=X'_{seg\_1}+X''_{seg\_2}$.

6. The ECG signal quality evaluation method based on the multi-scale convolutional and densely connected network according to claim 5, wherein in the step d-2), a batch size is set to 512 when the AlexNet model is trained by using the Adam optimizer based on the cross-entropy loss $L_{CE}$; and in the step d-3), a batch size is set to 512 when the AlexNet model is trained by using the Adam optimizer based on the cross-entropy loss $L_{CE}$.

7. The ECG signal quality evaluation method based on the multi-scale convolutional and densely connected network according to claim 1, wherein in the step e-2), the convolutional layer of the first convolution unit has a 1×7 convolution kernel, a step of 3, and 16 channels, the convolutional layer of the second convolution unit has a 1×5 convolution kernel, a step of 3, and 16 channels, the convolutional layer of the third convolution unit has a 1×3 convolution kernel, a step of 3, and 16 channels, and the average pooling layer has a 1×2 pooling kernel and a step of 2;

in the step e-3), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, wherein the second dilated convolutional layer has a 1×3 convolution kernel, 8 channels, a dilation rate of 1, and a step of 3; the third dilated convolutional layer has a 1×5 convolution kernel, 8 channels, a dilation rate of 2, and a step of 3, with a padding of 1; and the fourth dilated convolutional layer has a 1×7 convolution kernel, 8 channels, a dilation rate of 4, and a step of 3, with a padding of 1;

in the step e-4), the convolutional layer of the first convolution unit has a 1×7 convolution kernel, a step of 3, and 32 channels, the convolutional layer of the second convolution unit has a 1×5 convolution kernel, a step of 3, and 32 channels, the convolutional layer of the third convolution unit has a 1×3 convolution kernel, a step of 3, and 32 channels, and the average pooling layer has a 1×2 pooling kernel and a step of 2;

in the step e-5), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, wherein the second dilated convolutional layer has a 1×3 convolution kernel, 8 channels, a dilation rate of 1, and a step of 3, the third dilated convolutional layer has a 1×5 convolution kernel, 8 channels, a dilation rate of 2, and a step of 3, with a padding of 1, and the fourth dilated convolutional layer has a 1×7 convolution kernel, 8 channels, a dilation rate of 4, and a step of 3, with a padding of 1;

in the step e-6), the convolutional layer of the first convolution unit has a 1×7 convolution kernel, a step of 3, and 64 channels, the convolutional layer of the second convolution unit has a 1×5 convolution kernel, a step of 3, and 64 channels, the convolutional layer of the third convolution unit has a 1×3 convolution kernel, a step of 3, and 64 channels, and the average pooling layer has a 1×2 pooling kernel and a step of 2; and in the step e-7), the first dilated convolutional layer has a 1×1 convolution kernel, 16 channels, and a dilation rate of 2, and the multi-scale convolutional layer is sequentially constituted by a second dilated convolutional layer, a third dilated convolutional layer, and a fourth dilated convolutional layer, wherein the second dilated convolutional layer has a 1×3 convolution kernel, 8 channels, a dilation rate of 1, and a step of 3; the third dilated convolutional layer has a 1×5 convolution kernel, 8 channels, a dilation rate of 2, and a step of 3, with a padding of 1; and the fourth dilated convolutional layer has a 1×7 convolution kernel, 8 channels, a dilation rate of 4, and a step of 3, with a padding of 1.

8. The ECG signal quality evaluation method based on the multi-scale convolutional and densely connected network according to claim 1, further comprising: after the step e), training the improved lightweight densely connected quality classification model by using a cross-entropy loss function and a backpropagation algorithm.

9. The ECG signal quality evaluation method based on the multi-scale convolutional and densely connected network according to claim 8, wherein when the improved lightweight densely connected quality classification model is trained, an initial growth rate is set to 8 and a batch size is set to 512.

* * * * *